US007485448B2

(12) United States Patent
Yoshioka et al.

(10) Patent No.: US 7,485,448 B2
(45) Date of Patent: Feb. 3, 2009

(54) SERUM-FREE MEDIUM FOR PRODUCING RETROVIRUSES

(75) Inventors: Hirofumi Yoshioka, Otsu (JP); Yasushi Katayama, Otsu (JP); Daisuke Tomura, Otsu (JP); Masao Funakoshi, Otsu (JP); Kazuya Matsumoto, Otsu (JP); Junichi Mineno, Otsu (JP); Kazutoh Takesako, Otsu (JP); Ikunoshin Kato, Otsu (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 11/519,775

(22) Filed: Sep. 13, 2006

(65) Prior Publication Data

US 2007/0065854 A1     Mar. 22, 2007

(30) Foreign Application Priority Data

Sep. 13, 2005 (JP) ............................. 2005-265238

(51) Int. Cl.
 C12N 1/36 (2006.01)
 C12P 21/04 (2006.01)
(52) U.S. Cl. ..................................... 435/245; 435/70.1
(58) Field of Classification Search ....................... None
 See application file for complete search history.

(56) References Cited

U.S. PATENT DOCUMENTS

| 5,126,261 A | | 6/1992 | Morris et al. |
| 5,318,906 A | | 6/1994 | Sakata et al. |
| 6,060,317 A | * | 5/2000 | Malech ........................ 435/456 |
| 2002/0012954 A1 | * | 1/2002 | Sirbasku ..................... 435/7.23 |
| 2002/0034726 A1 | * | 3/2002 | Kanegasaki et al. ............ 435/4 |
| 2003/0228686 A1 | * | 12/2003 | Klausner et al. ............. 435/366 |

OTHER PUBLICATIONS

Gigout et al., Low calcium levels in serum-free media maintain chondrocyte phenotype in monolayer culture and reduce chondrocyte aggregation in suspension culture, 2005, Osteoarthritis and Cartilage, vol. 13, pp. 1012-1024.*
Zhao et al. Effect of calcium on aggregation and growth of 293 cells, 2005, Sheng Wu Gong Cheng Xue Bao, vol. 21, No. 3, abstract.*
King et al., Vaccinia Virus Growth Factor Stimulates Tyrosine Protein Kinase Activity of A431 Cell Epidermal Growth Factor Receptors, 1986, Molecular and Cellular Biology, vol. 6, No. 1, pp. 332-336.*
Sekhar, M. et al., "Retroviral Transduction of CD34-Enriched Hematopoietic Progenitor Cells Under Serum-Free Conditions"; Human Gene Therapy, vol. 7, pp. 33-38, Jan. 1, 1996.
Sekhar, M. et al., "Retroviral Transduction of CD34-Enriched Hematopoietic Progenitors using concentrated vector under Serum-Free conditions"; Gene Therapy, p. 358a, (1419), 1994.
Bello-Fernandez, C. et al., "Dendritic Cells Derived From CD34+ Progenitor Cells Under Serum-Free conditions can be efficiently transduced by a retroviral vector"; Retrovirus-Mediated Gene-Transfer and Expression; p. 429a, (1704), 1996.
Glimm, H. et al., "Efficient gene transfer into primitive Human Hematopoietic Progenitor Cells by a defined, high titer, non-concentrated vector containing medium produced under Serum-Free conditions"; Retrovirus-Mediated Gene Transfer and Expression; p. 432a, (1718), 1996.
Imbert, A.M. et al., "Use of Serum-Free medium for CD34+ Cells Transduction with retroviral supernatant"; Gene Transfer and Therapy; p. 894, (582) 1997.
Breems, D.A. et al., "Stroma-conditioned medium and sufficient prestimulation improve fibronectin fragment-mediated retroviral gene transfer into human primitive mobilized peripheral bloom stem cells through effects on their recovery and transduction efficiency"; Leukemia, 1998, vol. 12, pp. 951-959.
Bello-Fernandez, C. et al., "Efficient Retrovirus-Mediated Gene Transfer of Dendritic Cells generated from CD34+ Cord Blood Cells under Serum-Free conditions"; Human Gene Therapy; vol. 8, pp. 1651-1658, Sep. 20, 1997.
Sinacore, M.S. et al., "Adaptation of Mammalian Cells to Growth in Serum-Free Media"; Molecular Biotechnology, vol. 15, pp. 249-257, 2000.
A. E. Trickett et al., "Ex vivo expansion of functional T lymphocytes from HIV-infected individuals", Journal of Immunological Methods, vol. 262, No. 1-2, pp. 71-83, Apr. 1, 2002. XP004352176.
T. Okamoto et al., "Effects of insulin and transferrin on the generation of lymphokine-activated killer cells in serum-free medium", Journal of Immunological Methods, vol. 195, No. 1, pp. 7-14, Sep. 9, 1996.

(Continued)

*Primary Examiner*—Bruce Campell
*Assistant Examiner*—Benjamin P Blumel
(74) *Attorney, Agent, or Firm*—Browdy and Neimark, PLLC

(57) ABSTRACT

A method for obtaining a virus vector free of a serum, and a serum-free medium for cultivation of a virus producer cell which can be used for the method are provided. By cultivating a virus producer cell using a serum-free medium containing serum albumin, it is possible to cultivate the cell in a state equivalent to that in a serum-containing medium to produce a virus vector at a sufficient titer. The virus vector prepared from the virus producer cell cultivated in the medium exhibits gene transfer efficiency comparable to that of a conventional vector. The medium is useful for gene therapy and studies thereof.

8 Claims, 5 Drawing Sheets

OTHER PUBLICATIONS

D. P. Lennon et al., "A chemically defined medium supports in vitro proliferation and maintains the osteochondral potential of rat marrow-derived mesenchymal stem cells", Experimental Cell Research, vol. 219, No. 1, pp. 211-222, Jul. 1995. XP000981537.

Sigma-Aldrich, "Calcium in Cell Culture" [Online] 2007, XP002424538. Retrieved from the Internet: URL:http://www.sigmaaldrich.com/Area_of_Interest/Life_Science/Cell_Culture/Key_Resources/Media_Expert/Calcium.html#Calcium> [retrieved on Mar. 13, 2007].

C. Zhaolie et al., "A novel serum-free medium for the cultivation of vero cells on microcarriers", Biotechnology Techniques, vol. 10, No. 6, pp. 449-452, Jun. 1996. XP000900996.

J. M. Clark et al., "Serum supplements and serum-free media: Applicability for microcarrier culture of animal cells", Developments in Biological Standardization, vol. 50, pp. 81-91, 1982. XP000912273.

H. L. Malech, "Use of serum-free medium with fibronectin fragment enhanced transduction in a system of gas permeable plastic containers to achieve high levels of retrovirus transduction at clinical scale", Stem Cells, vol. 18, No. 2, pp. 155-156, 2000. XP002424539.

E. Conneally et al., "Efficient retroviral-mediated gene transfer to human cord blood stem cells with in vivo repopulating potential", Blood, vol. 91, No. 9, pp. 3487-3493, May 1, 1998. XP002424540.

P. A. Gerin et al., "Production of retroviral vectors for gene therapy with the human packaging cell line FLYRD18", Biotechnology Progress, vol. 15, No. 5, pp. 941-948, Sep. 1999. XP002424541.

O. W. Merten et al., "Evaluation of the new serum-free medium (MDSS2) for the production of different biologicals: Use of various cell lines", *Cytotechnology*, vol. 14, pp. 47-59, 1994.

Stem Technologies Inc., "BIT 9500, Serum Substitute for Colony Assays or Culture of Hematopoietic Cells", Product Information Sheet [Online], XP-002408652, pp. 1-2, Oct. 2003.

D. Farson et al., "Development and characterization of a cell line for large-scale, serum-free production of recombinant adeno-associated viral vectors", *The Journal of Gene Medicine*, vol. 6, pp. 1369-1381, Dec. 2004. XP-002408732.

T. Ueda et al., "Cloning and Functional Analysis of the Rhesus Macaque ABCG2 Gene", *The Journal of Biological Chemistry*, vol. 280, No. 2, pp. 991-998, Jan. 14, 2005. XP002408653.

M. C. Levesque et al., "Use of serum-free media to minimize apoptosis of chronic lymphocytic leukemia cells during in vitro culture", *Leukemia: Official Journal of the Leukemia Society of America, Leukemia Research Fund*, United Kingdom, vol. 115, No. 8, pp. 1305-1307, Aug. 2001. XP-002408654.

\* cited by examiner

Medium I | Medium II | Medium III

SERUM-FREE MEDIUM FOR PRODUCING RETROVIRUSES

BACKGROUND OF THE INVENTION

1. Field of the Invention

The present invention relates to a novel serum-free tissue culture medium useful for cultivation of a virus producer cell, in particular a retrovirus producer cell required for production of a recombinant retrovirus vector, which is used for studies of gene therapy or clinical gene therapy, and a method for producing a virus, in particular a recombinant retrovirus vector, using the medium.

2. Description of Related Art

Gene therapies in which virus vectors are used have been developed and many clinical tests have been carried out aiming at treatment of congenital genetic diseases as well as cancers and infectious diseases. In particular, a large number of trials have been conducted for gene therapy utilizing a retrovirus vector or a adenovirus vector.

Examples of DNA vectors used for production of recombinant retrovirus vectors which are used for integrating genes of interest include MFG and LXSN (GenBank Accession No. M28248) in which genes for virus particle structural proteins (gag, pol, env) are eliminated from the wild-type Moloney murine leukemia virus (MoMLV)) genome. Other vectors having further modification have been used in clinical tests for human subjects.

A recombinant retrovirus vector is produced by cultivating a producer cell which is derived from transfection of a DNA vector inserted with a gene of interest into a packaging cell (Psi-Crip, GP+E86, GP+envAm12, PG13, etc.), and collecting a supernatant which contains the virus vector of interest. A producer cell clone that stably produces a retrovirus vector for stable expression of a gene of interest may be selected, for example, from infected cells obtained by further infecting a packaging cell using the supernatant. Through such steps, a master cell bank (MCB) and a working cell bank (WCB) are prepared, and a recombinant retrovirus vector for gene therapy is stably produced.

Cultivation of a retrovirus producer cell is very important for stable retrovirus production. Usually, a retrovirus producer cell is cultivated in a serum-containing medium, and a virus-containing supernatant is collected from the culture. A case of successful cultivation under serum-free conditions has been reported. In this case, a cell capable of growing under serum-free conditions is selected in a step called adaptation in which the serum concentration in the medium is gradually decreased. However, it is generally very difficult to produce a retrovirus using a serum-free medium (Mol. Biotechnol., 15:249-257 (2000)).

SUMMARY OF THE INVENTION

Use of an animal serum has great risk, for example, because it may contain an unknown virus. Therefore, it is desirable to use a serum-free medium for cultivation of a retrovirus producer cell. Thus, a serum-free medium which does not contain an animal serum is used only in the final virus production step upon production of a recombinant retrovirus vector to be clinically administered to humans in many cases. Furthermore, selection of the lot of a serum to be used is very important because productivity of a recombinant retrovirus vector greatly varies among serum lots. On the other hand, such variation in productivity can be suppressed if a serum-free medium is used. Therefore, the use of a serum-free medium is highly necessary. Several serum-free media for virus production are commercially available although none of them can serve as a substitute for a serum-containing medium. Attempts have been made for preparing a retrovirus vector free of a serum as follows. In one method, after cultivation in a serum-containing medium, the medium is exchanged for a serum-free medium such as X-VIVO15 (Cambrex) in the final virus collection step and a virus supernatant is then collected from the culture. In another method, a cell that can be cultivated under serum-free conditions is selected by adaptation. However, they still are not sufficiently effective.

As a result of intensive studies, the present inventors have shown that a retrovirus producer cell can grow well in a serum-free medium containing serum albumin. The present inventors have further found that a high-titer retrovirus supernatant can be collected using the medium. Thus, the present invention has been completed.

In summary, the present invention relates to the following.

[1] A serum-free medium used for cultivation of a virus producer cell, which contains serum albumin.

[2] The medium according to [1], wherein the serum albumin is human serum albumin.

[3] The medium according to [1], which contains the serum albumin at a concentration of 0.05 to 1% by weight.

[4] The medium according to [1], which contains interleukin-2.

[5] The medium according to [4], which contains interleukin-2 at a concentration of 10 to 1000 JRU/ml.

[6] The medium according to [1], which contains calcium at a concentration of 1.35 to 6.31 mmol/L.

[7] The medium according to [1], which contains epidermal growth factor.

[8] The medium according to [1], wherein the virus producer cell is a recombinant retrovirus vector producer cell.

[9] A method for producing a substance of interest, the method comprising cultivating a cell capable of producing a substance of interest in the medium defined by [1].

[10] The method according to [9], wherein the cultivation is initiated by inoculating a stock of the cell capable of producing a substance of interest into the medium defined by [1].

[11] The method according to [9], wherein the substance of interest is a recombinant retrovirus vector.

Using the medium of the present invention, it is possible to readily prepare a recombinant retrovirus vector free of a serum and a therapeutic composition containing the vector. The composition is very useful in the field of gene therapy.

DETAILED DESCRIPTION OF THE INVENTION

Figure 1:
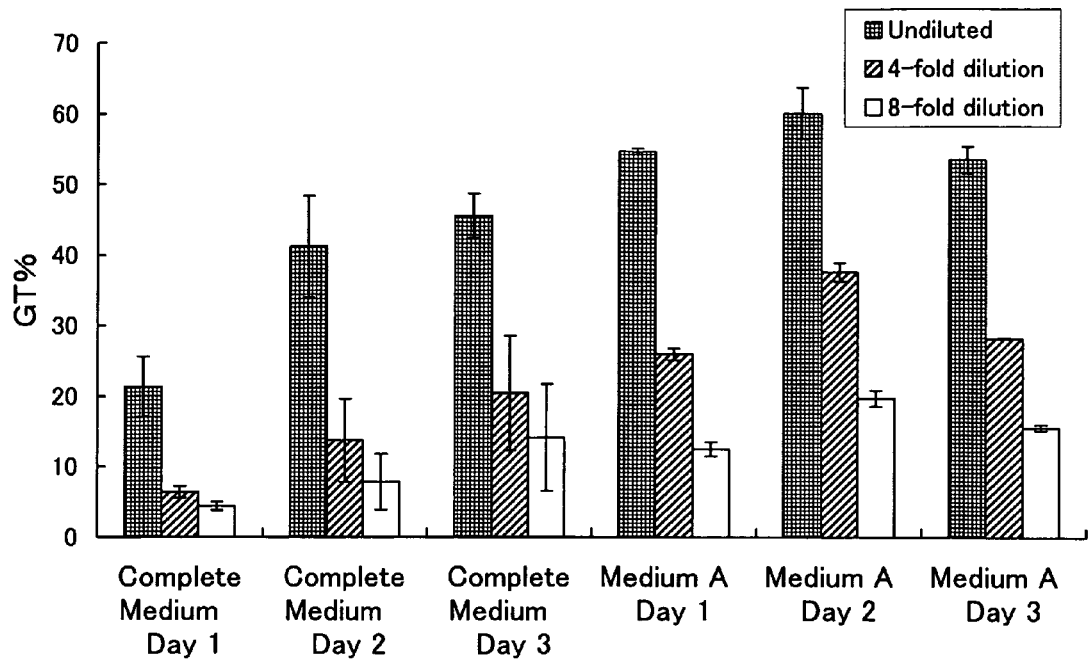
FIG. 1 illustrates the efficiency of gene transfer into CEM cells with retroviruses obtained using the complete medium or the medium A.

The first aspect of the present invention relates to a serum-free medium which is suitable for cultivation of a virus producer cell.

This medium is one prepared by adding serum albumin to a basic medium free of a serum that is prepared by mixing components necessary for cultivation of a virus producer cell.

The components of the basic medium include: energy sources such as amino acids, saccharides and organic acids; vitamins; buffer components for pH adjustment; and inorganic salts. The medium may contain a pH indicator such as phenol red. A known medium free of a serum such as DMEM, IMDM or Ham's F12 medium may be used as the basic medium. These media are available as commercial products from Invitrogen, Sigma and the like. Commercially available serum-free media such as Opti-ProSFM, VP-SFM and 293SFMII (all from Invitrogen), and HyQ SFM4MegaVir (HyClone) may also be used.

The medium of the present invention can be prepared by adding serum albumin to the above-mentioned medium free of a serum. Although it is not intended to limit the present invention, human serum albumin as a plasma fractionation product (e.g., a human albumin formulation) is preferably used according to the present invention. The final concentration of the added serum albumin is 0.05 to 1%, preferably 0.1 to 0.3%. Some commercially available human serum albumin formulations contain sodium N-acetyl-tryptophan and sodium caprylate as stabilizing agents. They may be contained in the serum-free medium although it is not intended to limit the present invention. The content of sodium N-acetyl-tryptophan is 10 to 200 mg/L, preferably 40 to 50 mg/L. The content of sodium caprylate is 10 to 100 mg/L, preferably 25 to 30 mg/L. Furthermore, interleukin-2, preferably recombinant human interleukin-2, is preferably added to the medium of the present invention. The final concentration of the added interleukin-2 is 10 to 1000 JRU/mL, preferably 50 to 500 JRU/mL. In addition, the medium of the present invention can contain calcium at a concentration of 1.35 to 6.31 mmol/L, preferably 2.70 to 4.51 mmol/L. The above concentrations correspond to 150 to 700 mg/L and 300 to 500 mg/L, respectively, when calcium chloride is used as calcium.

A purified protein (natural or recombinant) such as transferrin, insulin or epidermal growth factor, oleic acid, progesterone or the like may be added to the medium of the present invention to increase the cell growth and/or the titer of produced virus. If epidermal growth factor is to be added to the medium, the concentration is 2 to 30 mg/L, preferably 5 to 20 mg/L.

Although there is no specific limitation concerning the virus producer cell to be cultivated using the medium of the present invention, the medium of the present invention is preferably used for cultivating a retrovirus vector producer cell.

The second aspect of the present invention relates to a method for producing a substance of interest such as a virus vector. In a preferred embodiment of the present invention, a frozen stock (e.g., a MCB or a WCB) of a virus producer cell for producing a recombinant virus vector is thawed using an appropriate means, it is directly inoculated into the serum-free medium of the present invention to initiate cultivation, and it is then possible to allow the cell to grow. For preparation of a recombinant virus vector in large quantities, it is preferable to comprise a step of adapting a virus producer cell to the serum-free medium of the present invention. For example, for adapting a cell that has been cultivated in a medium containing a serum at a concentration of 10% to the serum-free medium, this step is carried out as follows: cultivation is carried out using a serum-free medium to which a serum is added at a concentration of 5%; the cell is passaged 2 to 4 times for adaptation; and adaptation cultivation is similarly carried out using a serum-free medium to which a serum is added at a concentration lowered to 2%. The cell is adapted finally to the serum-free medium by decreasing the serum concentration in a stepwise manner as described above.

Although there is no specific limitation concerning the virus vector produced according to the present invention, a particularly preferable example is a retrovirus vector or a recombinant retrovirus vector.

There is no specific limitation concerning the retrovirus vector produced according to the present invention. A replication-defective retrovirus vector with which unlimited infection or gene transfer is prevented is usually used according to the present invention. Examples of known replication-defective retrovirus vectors include retrovirus vectors (e.g., MFG vector, α-SGC vector (WO 92/07943), pBabe (Nucleic Acids Research, 18:3587-3596 (1990)), pLXIN (Clontech) or pDON-AI (Takara Bio)), lentivirus vectors (human immunodeficiency virus (HIV)-derived vectors, simian immunodeficiency virus (SIV)-derived vectors, etc.) and modifications thereof.

The retrovirus vector may carry an arbitrary foreign gene. Examples of the foreign genes include genes encoding polypeptides (enzymes, growth factors, cytokines, receptors, structural proteins, etc.), antisense RNAs, ribozymes, decoys, and RNAs that cause RNA interference. An appropriate promoter, an enhancer, a terminator or other transcription regulatory elements may be inserted into the vector for controlling the expression of the foreign gene.

According to the present invention, a retrovirus vector is produced by cultivating, in the medium of the present invention, a retrovirus producer cell which is constructed by transferring a DNA encoding the retrovirus vector into a retrovirus packaging cell line.

There is no specific limitation concerning the packaging cell line. A known packaging cell line such as PG13 (ATCC CRL-10686), PA317 (ATCC CRL-9078), GP+E-86 or GP+envAm-12 (U.S. Pat. No. 5,278,056) or Psi-Crip (Proc. Natl. Acad. Sci. USA, 85:6460-6464 (1988)) can be used. Alternatively, a retrovirus producer cell can be constructed by transferring a packaging plasmid carrying genes necessary for production of retrovirus particles (Retrovirus Packaging Kit (Takara Bio), etc.) into 293 cell or 293T cell of which the transfection efficiency is high.

A retrovirus producer cell can be cultivated under normal cultivated conditions. For example, cultivation may be carried out with humidity of 95% and $CO_2$ concentration of 5% although it is not intended to limit the present invention. For example, cultivation can be carried out at a temperature of 30 to 37° C. The cell may be cultivated at a temperature out of this range provided that the desired cell growth and retrovirus vector production can be achieved. According to the present invention, a retrovirus is produced by collecting a supernatant from the thus obtained culture. A retrovirus vector may be prepared as the supernatant as it is, a filtrate obtained by filtrating the supernatant through a filter, or a retrovirus vector obtained by concentrating or purifying the supernatant according to a known method. It is stored until use using an appropriate means (e.g., freezing). A retrovirus vector at a higher titer than a conventional one can be obtained by cultivating a retrovirus producer cell using the medium of the present invention as described above.

EXAMPLES

The following Examples illustrate the present invention in more detail, but are not to be construed to limit the scope thereof.

Example 1

Preparation of Medium

A medium A was prepared by adding 8 mL of 25% human serum albumin (Buminate 25%, Baxter) which contained 2 g of human serum albumin, 42.92 mg of sodium N-acetyl-tryptophan, and 26.6 mg of sodium caprylate to 1 L of a commercially available medium GT-T503 (Takara Bio). A medium B was prepared by further adding interleukin-2 (Pro-leukin, Chiron) at a final concentration of 175 JRU/mL to the medium A.

Example 2

1. Cultivation of Retrovirus Producer Cell

A working cell bank (WCB) of a mouse retrovirus producer cell expressing a gene for human low-affinity nerve growth factor receptor lacking its intracellular domain (ΔLNGFR) constructed using GP+envAm-12 as a packaging cell was thawed in a water bath at 37° C. The thawed cell suspension was transferred into a 15-mL centrifuge tube. 10 mL of a complete medium (DMEM medium (Cambrex) containing 10% fetal calf serum (JRH)) was further added thereto. The mixture was centrifuged at 500×g for 5 minutes at 20° C. After centrifugation, a supernatant was removed, the cells were suspended in the complete medium (DMEM medium containing 10% fetal calf serum), and the cells were counted. After counting, $1 \times 10^6$ of the cells were dispensed into each of 15-mL centrifuge tubes. The tubes were centrifuged at 500×g for 5 minutes at 20° C. After centrifugation, a supernatant was removed. The cells were then suspended in the medium A, and cultivated using T25 cell culture flasks (CELLBIND, Corning) in a $CO_2$ incubator (temperature: 37° C.; humidity: 95%; $CO_2$ concentration: 5%). Cultivation using the complete medium was carried out as a control for comparison. For both the complete medium and the medium A, cells were passaged at intervals of three days by seeding at a cell density of $2 \times 10^4/cm^2$. The cells were passaged three times under the conditions.

2. Collection of Retrovirus Supernatant

The cells were cultivated for three days after the third passage, and passaged for retrovirus collection in a similar manner. The cells were seeded at a cell density of $4 \times 10^4/cm^2$. Cultivation was carried out from day 0 to day 1 in a $CO_2$ incubator (temperature: 37° C.; humidity: 95%; $CO_2$ concentration: 5%). On day 1, the complete medium or the medium A was removed, and exchanged for a fresh medium. The volume was adjusted to 0.1 mL/cm$^2$ for virus collection. Cultivation was carried out while lowering the temperature of the $CO_2$ incubator to 33° C. On day 2, a supernatant was collected from each culture flask. The flask was supplemented with the complete medium or the medium A, and cultivation was carried out. The collection was carried out for successive three days. The collected culture supernatants (Day 1, Day 2 and Day 3) were filtrated through filters with a pore size of 0.22 μm (Millipore) to obtain retrovirus supernatants, which were divided into aliquots and stored at −80° C.

3. Assessment of Retrovirus Supernatant for Gene Transfer

Gene transfer efficiency was measured using the retrovirus supernatants obtained by cultivation and collection using the complete medium or the medium A as described above. The undiluted supernatants, 4-fold dilutions and 8-fold dilutions were prepared for the respective retrovirus supernatants collected using the complete medium or the medium A. Protamine (Mochida Pharmaceutical) was further added at a final concentration of 4 μg/mL, respectively. The complete medium or the medium A was used for dilution. $0.5 \times 10^6$ cells of human leukemia cell CEM were added to and suspended in 500 μL of the dilution. The suspension was transferred into a 24-well cell culture plate (Asahi Techno Glass). The 24-well cell culture plate was centrifuged at 32° C. at 1000×g for 2 hours. After centrifugation, a supernatant was removed from each well, and a medium for CEM (RPMI1640 medium containing 10% serum, Cambrex) was added to each well. After suspending, the cells were cultivated in a $CO_2$ incubator (temperature: 37° C.; humidity: 95%; $CO_2$ concentration: 5%) for three days. After cultivation, the efficiency of gene transfer with the retrovirus was determined by examining the expression of the gene for human low-affinity nerve growth factor receptor (ΔLNGFR) as a marker gene of the retrovirus vector using a fluorescently labeled antibody that recognizes LNGFR. After infection and cultivation, $0.5 \times 10^6$ of the cells were transferred into an Eppendorf tube, and precipitated by centrifugation at 4° C. at 500×g for 5 minutes. After removing a supernatant, 100 μL of PBS solution containing 0.5 μg of a monoclonal antibody that recognizes ΔLNGFR (Chemicon) as a primary antibody was added to the precipitated cells. The suspension was allowed to stand on ice for 20 minutes. A sample was prepared using mouse IgG (Becton-Dickinson) as an isotype control for determining nonspecific binding (background). Then, 900 μL of a pre-chilled phosphate buffer solution (PBS, Gibco) was added thereto, and the cells were precipitated by centrifugation at 4° C. at 500×g for 5 minutes. After removing a supernatant, 100 μL of phycoerythrin (PE)-labeled anti-mouse IgG antibody (Dako) as a secondary antibody that recognizes the primary antibody was added to the precipitated cells. The suspension was allowed to stand on ice for 20 minutes. Then, 900 μL of a pre-chilled phosphate buffer solution (PBS, Gibco) was added thereto, and the cells were precipitated by centrifugation at 4° C. at 500×g for 5 minutes. After removing a supernatant, a 3% formaldehyde solution was added to the precipitated cells for fixation. After fixation, flow cytometry analysis (FCM) was carried out.

The flow cytometry analysis was carried out using FACS Caliber (Becton-Dickinson) according to the instructions attached to the instrument. The ratio of ΔLNGFR expression was determined as follows: a region of fluorescence intensity for cells not expressing ΔLNGFR in the histogram of PE detection parameters (x axis: intensity of fluorescence from PE; y axis: cell number) was confirmed using the isotype control; a region of fluorescence intensity for cells expressing ΔLNGFR without the above region was determined; and the ratio (%) was determined. After the determination, the transfer efficiency (GT (%): Gene Transduction efficiency) was calculated according to the following equation:

$$GT(\%) = \text{measured value for each sample} - \text{measured value for isotype control (background)}$$

The results of gene transfer efficiency measurements are shown in FIG. 1.

As shown in FIG. 1, the gene transfer efficiency observed using the retrovirus supernatant collected on each day after cultivation using the medium A was equivalent to or higher than the gene transfer efficiency with the complete medium. Thus, it was shown that a virus at a higher titer than that obtained using the complete medium was obtained. These results show that passaging and virus collection can be sufficiently carried out by cultivation from a working cell bank without adaptation.

Example 3

1. Preparation of Retrovirus Vector

A retrovirus vector plasmid pDOG-polII was constructed as follows. First, an rsGFP expression vector pQBI25 (Qbiogene Inc.) was cleaved with restriction enzymes NheI and NotI to obtain a 775-bp GFP gene fragment. Next, pQBI polII (Qbiogene Inc.) was cleaved with restriction enzymes NheI and NotI to remove an rsGFP-NeoR fusion gene. The previously obtained 775-bp rsGFP gene fragment was inserted thereinto to obtain a vector pQBI polII(neo-) in which the rsGFP gene is expressed under the control of polII promoter. pQBI polII(neo-) was digested with a restriction enzyme XhoI to obtain a DNA fragment containing a GFP expression unit under the control of polII promoter. The termini were blunted using DNA blunting kit (Takara Bio). Termini of a 4.58-kbp vector fragment obtained by digesting a retrovirus vector plasmid pDON-AI (Takara Bio) with restriction enzymes XhoI and SphI were blunted using DNA blunting kit (Takara Bio), and then dephosphorylated using alkaline phosphatase (Takara Bio). The previously blunted DNA fragment containing the rsGFP expression unit under the control of polII promoter was inserted into this blunted vector using DNA Ligation Kit (Takara Bio) to obtain an rsGFP expression recombinant retrovirus vector pDOG-polII.

Transient virus production was carried out using the vector pDOG-polII and Retrovirus Packaging Kit Eco (Takara Bio) to obtain an ecotropic virus DOG-polII. The thus obtained ecotropic virus DOG-polII was used to infect a GaLV retrovirus packaging cell PG13 (ATCC CRL-10686) in the presence of RetroNectin (Takara Bio) to obtain a gene-transferred cell PG13/DOG-polII.

2. Assessment of Retrovirus Vector Productivity

PG13/DOG-polII cell was cultivated using the medium A or the complete medium according to the method as described in Example 2 to prepare a retrovirus supernatant. The thus obtained retrovirus supernatant was used to carry out gene transfer into human fibrosarcoma cell HT1080.

The undiluted supernatants, 4-fold dilutions, 20-fold dilutions and 100-fold dilutions were prepared for the retrovirus supernatants collected using the complete medium or the medium A on day 3. Protamine (Mochida Pharmaceutical) was further added at a final concentration of 4 µg/mL. The complete medium or the medium A was used for dilution. After removing the culture, 1 mL of the dilution was added 1×10$^5$ cells of human fibrosarcoma cell HT1080 which had been inoculated on the day before the infection. The cells were allowed to stand in a $CO_2$ incubator (temperature: 37° C.; humidity: 95%; $CO_2$ concentration:. 5%) for six hours. A sample was prepared by adding only the medium as a negative control. Then, a virus supernatant was removed from each well, a medium for HT1080 cell (DMEM medium containing 10% serum) was added thereto, and the cells were cultivated for three days.

After cultivation, intracellular rsGFP expression was measured by flow cytometry (FCM) in order to determine the efficiency of gene transfer with the retrovirus. The flow cytometry analysis was carried out using FACS Caliber according to the instructions attached to the instrument. The ratio of rsGFP expression was determined as follows: a region of fluorescence intensity for cells not expressing rsGFP in the histogram of FITC detection parameters (x axis: intensity of fluorescence from rsGFP; y axis: cell number) was confirmed using the negative control; a region of fluorescence intensity for cells expressing rsGFP without the above region was determined; and the ratio (%) was determined. After the determination, the transfer efficiency was calculated according to the following equation:

$$GT(\%) = \text{measured value for each sample} - \text{measured value for negative control (background)}$$

Figure 2:
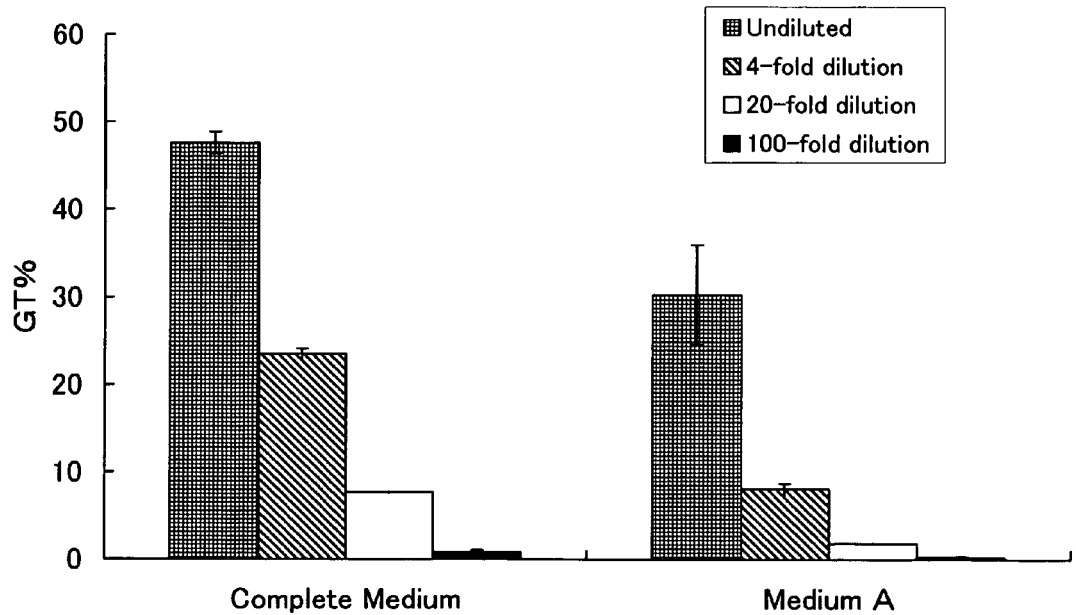
FIG. 2 illustrates the efficiency of gene transfer into HT1080 cells with retroviruses obtained using the complete medium or the medium A.

The results of gene transfer efficiency measurements are shown in FIG. 2.

As shown in FIG. 2, also using the gibbon ape retrovirus producer cell, the gene transfer efficiency observed for the retrovirus supernatant collected from the culture obtained using the medium A was comparable to that with the complete medium. These results show that passaging and virus collection can be sufficiently carried out by cultivation directly in a serum-free medium from a working cell bank without adaptation.

Example 4

A virus supernatant was prepared using a mouse retrovirus producer cell expressing a gene for ΔLNGFR according to the method as described in Example 2. The medium A or a medium B which was prepared by adding IL-2 to the medium A at a concentration of 600 JRU/mL was used. Cultivation was carried out as described in Example 2-1 except that the cells were passaged five times. Virus collection was carried out as described in Example 2-2 except that the cells were seeded at a cell density of 6×10$^4$/cm$^2$. For assessment of gene transfer efficiency, in addition to CEM cells, human peripheral blood mononuclear cells (PBMCs) were subjected to gene transfer and FACS measurement in a similar manner.

The results of cell growth ratios are shown in Table 1. For both of the medium A and the medium B, the growth ratios in P0 (passage 0, and so on) and P1 were about 3-fold probably because the cells were gradually adapting. The growth ratios were 5-fold or more during and after P3. Among the media, a better growth ratio of 7469-fold (P0-P5) was observed using the medium B which contained IL-2 as compared with the growth ratio of 5228-fold (P0-P5) with the medium A.

TABLE 1

| | Cell growth ratio | | | | | | |
|---|---|---|---|---|---|---|---|
| Medium | P0 | P1 | P2 | P3 | P4 | P5 | P0-P5 |
| A | 2.69 | 3.28 | 4.18 | 5.24 | 4.68 | 5.78 | 5228 |
| B | 2.75 | 3.28 | 4.96 | 4.64 | 6.84 | 5.26 | 7469 |

Figure 3:
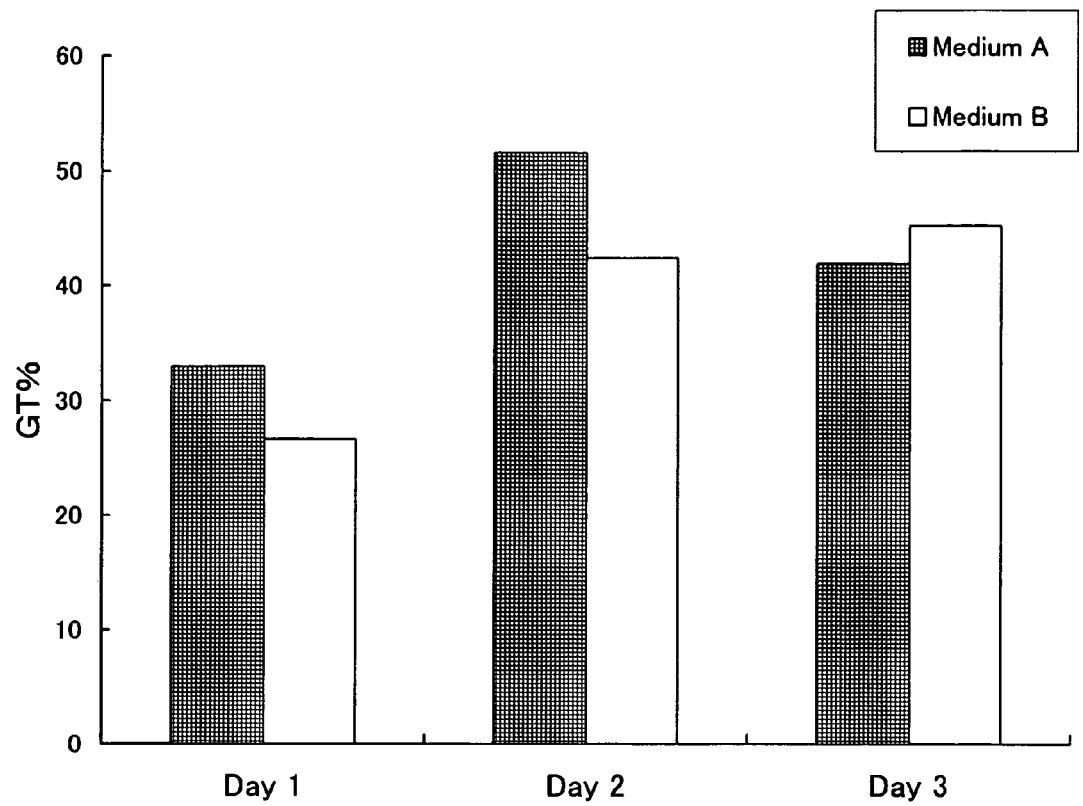
FIG. 3 illustrates the efficiency of gene transfer into CEM cells with retroviruses obtained using the medium A or the medium B.
Figure 4:
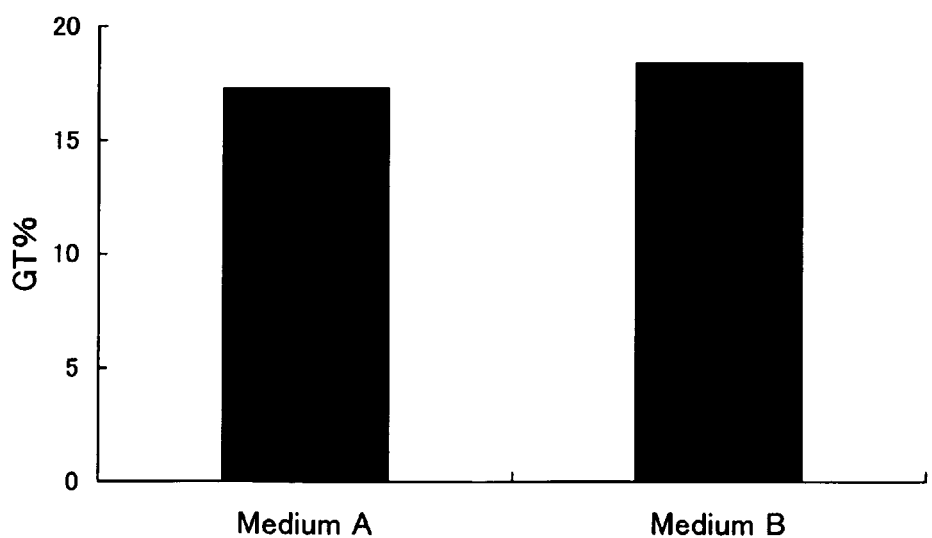
FIG. 4 illustrates the efficiency of gene transfer into human PBMCs with retroviruses obtained using the medium A or the medium B.

The results of gene transfer efficiency using the undiluted retrovirus supernatants are shown in FIGS. 3 and 4. Equivalent gene transfer efficiency was observed using the medium A and the medium B upon both the gene transfer into CEM cells (FIG. 3) and the gene transfer into human PBMCs (FIG. 4).

Example 5

Comparison with Commercially Available Serum-free Media

The medium A of the present invention was compared with various commercially available serum-free media using a mouse retrovirus producer cell expressing a gene for ΔLNGFR according to the method as described in Example 2. Cultivation was carried out in two ways, i.e., direct adaptation and indirect adaptation.

(1) Direct adaptation: A working cell bank was passaged twice in the complete medium. The medium was then exchanged directly for the medium A or a commercially available serum-free medium. The cells were passaged four times.

(2) Indirect adaptation: A working cell bank was passaged twice in the complete medium. Adaptation cultivation was carried out while lowering the fetal calf serum concentration in a stepwise manner (the fetal calf serum concentration: 6.6%→3.3%→1.5%→0%).

The following four media were used:
1. The medium A
2. AIM-V (Invitrogen)
3. HyQ SFM4MegaVir (HyClone)
4. Opti-ProSFM (Invitrogen)

The recommended amounts of glutamine were added to the media 3 and 4.

Virus collection was carried out as described in Example 2-2. Gene transfer was carried out using CEM cells. Gene transfer efficiency was assessed as described in Example 2-3.

(1) According to the direct adaptation, the cells could be passaged four times only using the medium A or Opti-ProSFM. In particular, the growth during the fourth passage with the medium A was superior. The cells could not be cultivated in other commercially available serum-free media. The cultivation with the medium AIM-V or the medium HyQ SFM4MegaVir was terminated during the second passage.

(2) According to the indirect adaptation, the fetal calf serum concentrations could be lowered to 0% with the medium A or Opti-ProSFM. The fetal calf serum concentration could be lowered only to 1.5% with the medium AIM-V and to 6.6% with the medium HyQ SFM4MegaVir. Thus, cultivation under serum-free conditions could not be accomplished.

Next, gene transfer efficiency was assessed for the cases of the medium A and Opti-ProSFM with which virus collection could be carried out according to the indirect adaptation. The results are shown in Table 2. The gene transfer efficiency observed with the medium A was about 2-fold higher than that observed with Opti-ProSFM.

Based on these results, it was confirmed that the medium A of the present invention is superior in respect of cultivation of a retrovirus producer cell to commercially available serum-free media, and retrovirus production can carried out clearly with high efficiency.

TABLE 2

| | Gene transfer efficiency (GT (%)) | | |
|---|---|---|---|
| | Undiluted | 4-fold dilution | 16-fold dilution |
| Medium A | 50.82% | 12.25% | 1.92% |
| Opti-ProSFM | 31.53% | 6.62% | 1.1% |

Example 6

Improvement in Cell Growth Due to Addition of Serum Albumin

Cell cultivation was carried out using a mouse retrovirus producer cell expressing a gene for ΔLNGFR according to the method as described in Example 2. After cell cultivation was initiated using the medium A, cells were cultivated from the first passage using the medium A or a commercially available medium GT-T503 (Takara Bio). The cells were passaged once more using the same medium, and the cell growth ratios were compared with each other.

The results of cell growth ratios are shown in Table 3. The cell growth ratio observed using the medium A which contained human serum albumin was about 2-fold higher than that observed using the medium GT-T503. The conditions of the cells in the medium GT-T503 were not well because many cells were aggregated or detached.

TABLE 3

| | Cell growth ratio | |
|---|---|---|
| | 1st to 2nd passage | 2nd to 3rd passage |
| Medium A | 4.18 | 5.24 |
| Medium GT-T503 | 2.5 | 2.14 |

Example 7

Assessment of Effect of Serum Albumin Added to Commercially Available Serum-free Medium A virus supernatant was prepared using a mouse retrovirus producer cell expressing a gene for ΔLNGFR according to the method as described in Example 2. A commercially available serum-free medium Opti-ProSFM (Invitrogen) and a medium prepared by adding 25% human serum albumin (Buminate 25% (HSA), Baxter) to result in a final concentration of 0.2% by weight to Opti-ProSFM were used in this Example. The recommended amount of glutamine was added to Opti-ProSFM.

Cultivation was carried out as described in Example 2-1 except that the cells were passaged five times. Virus collection was carried out as described in Example 2-2. Collection on day 4 was carried out also as described in Example 2-2.

Gene transfer was carried out using CEM cells. Gene transfer efficiency was assessed as described in Example 2-3.

Figure 5:
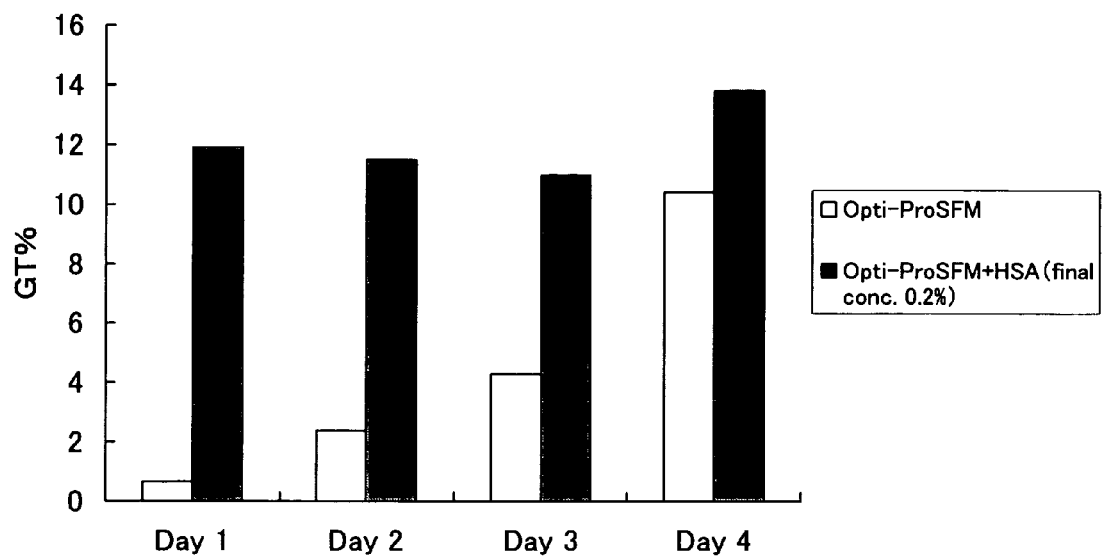
FIG. 5 illustrates the efficiency of gene transfer into CEM cells with retroviruses obtained using Opti-ProSFM or Opti-ProSFM +HSA (at a final concentration of 0.2%).

The results of gene transfer efficiency observed with 4-fold dilutions of the retrovirus supernatants are shown in FIG. 5.

As shown in FIG. 5, the virus titer was increased by the addition of human serum albumin (HSA).

Example 8

Examination of Calcium Concentration in Medium

A virus supernatant was prepared using a mouse retrovirus producer cell expressing a gene for ΔLNGFR according to the method as described in Example 2. A medium I in which transferrin was eliminated from the medium A, as well as a medium II and a medium III in which the calcium concentration in the medium I was adjusted from 165 mg/L (the original concentration) to 330 mg/L and 495 mg/L, respectively, by adding calcium chloride according to Pharmacopeia of Japan were used in this Example. Cultivation was carried out as described in Example 2-1 except that the cells were passaged five times. Virus collection was carried out as described in Example 2-2. Gene transfer was carried out using CEM cells. Gene transfer efficiency was assessed as described in Example 2-3.

Figure 6:
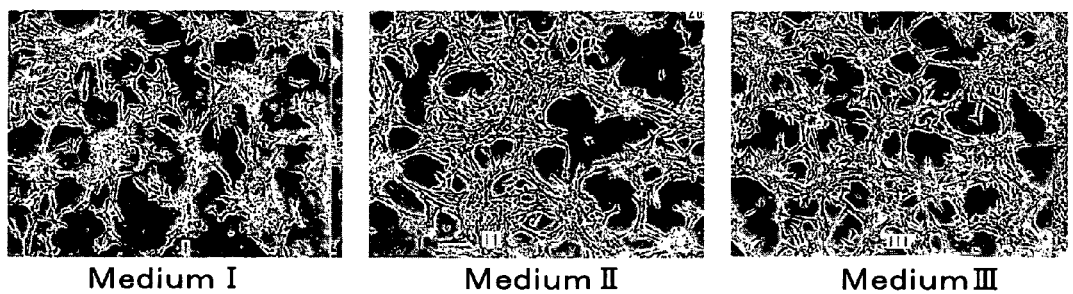
FIG. 6 shows the morphologies of the cells on Day 3 of virus collection.
Figure 7:
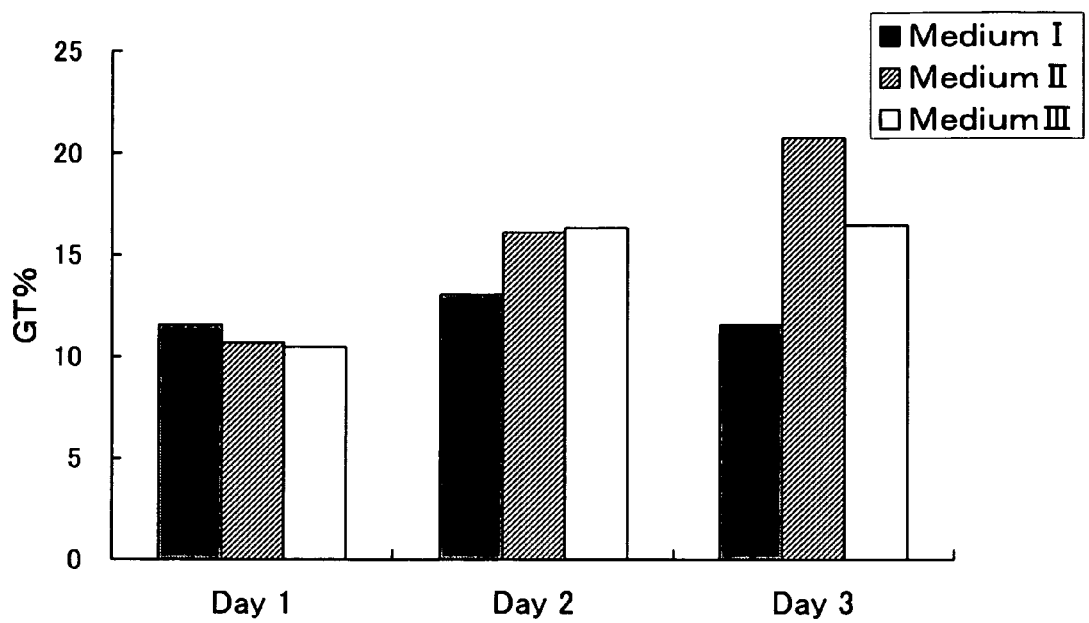
FIG. 7 illustrates the efficiency of gene transfer into CEM cells with retroviruses obtained using the medium I, the medium II or the medium III.

FIG. 6 is a photograph that shows the morphologies of the cells on Day 3 of virus collection. The results of gene transfer efficiency are shown in FIG. 7. In the preliminary test, equivalent gene transfer efficiency was observed using the medium I and a medium in which the calcium concentration in the medium I was adjusted to 640 mg/L. By increasing the calcium concentration from 165 mg/L (the original concentration) to 330 or 495 mg/L, the number of aggregated or detached cells of the mouse retrovirus producer cell expressing a gene for ΔLNGFR was reduced (FIG. 6) and virus collection could be carried out for three successive days. The virus titers reflected the conditions of the cells. That is, the collected virus tended to decrease (Day 1>Day2>Day3 of virus collection) using the medium I, while the collected virus tended to increase using the medium II and the medium III (FIG. 7). Thus, the successive collection which is necessary for retrovirus collection could be carried out by increasing the calcium concentration. Furthermore, the reduction in cells detached in the virus supernatant eliminated clogging upon subsequent filtration and facilitated the procedure.

Example 9

Assessment of Effect of Added Epidermal Growth Factor

A virus supernatant was prepared using a mouse retrovirus producer cell expressing a gene for ΔLNGFR according to the method as described in Example 2. The medium I in which transferrin was eliminated from the medium A and a medium IV prepared by adding epidermal growth factor (Wako Pure Chemical Industries) to the medium I at a final concentration of 10 mg/L were used in this Example. Cultivation was carried out as described in Example 2-1 except that the cells were passaged five times. Virus collection was carried out as described in Example 2-2. Gene transfer was carried out using CEM cells. Gene transfer efficiency was assessed as described in Example 2-3.

Figure 8:
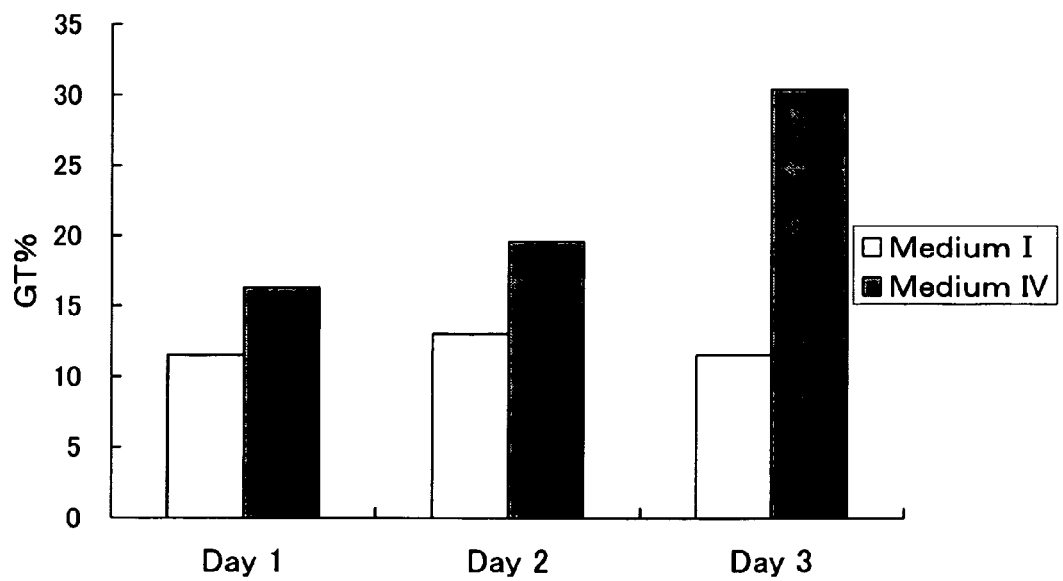
FIG. 8 illustrates the efficiency of gene transfer into CEM cells with retroviruses obtained using the medium I or the medium IV.

The results of gene transfer efficiency are shown in FIG. 8. As shown in FIG. 8, the virus titer was increased by the addition of epidermal growth factor.

Example 10

Assessment of Synergistic Effect of Modified Calcium Concentration and Added Epidermal Growth Factor A virus supernatant was prepared using a mouse retrovirus producer cell expressing a gene for ΔLNGFR according to the method as described in Example 2. The medium A and a medium V in which the calcium concentration in the medium A was adjusted from 165 mg/L (the original concentration) to 330 mg/L by adding calcium chloride according to Pharmacopeia of Japan and to which epidermal growth factor was added at a final concentration of 10 mg/L were used in this Example. Cultivation was carried out as described in Example 2-1 except that the cells were passaged five times. Virus collection was carried out as described in Example 2-2. Gene transfer was carried out using CEM cells. Gene transfer efficiency was assessed as described in Example 2-3.

Figure 9:
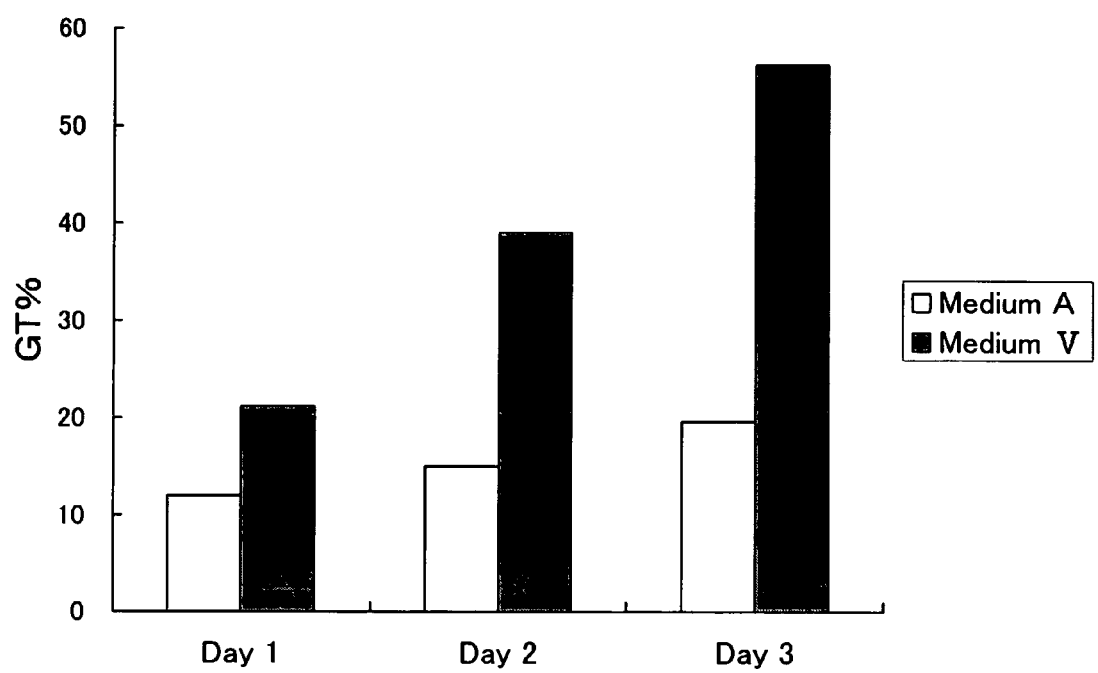
FIG. 9 illustrates the efficiency of gene transfer into CEM cells with retroviruses obtained using the medium A or the medium V.

The results of gene transfer efficiency are shown in FIG. 9. The virus titer was increased by 3-fold by modifying the calcium concentration from 165 mg/L (the original concentration) to 330 mg/L and adding epidermal growth factor. Furthermore, the successive collection which is necessary for retrovirus collection could be carried out. In addition, the reduction in cells detached in the virus supernatant eliminated clogging upon subsequent filtration and facilitated the procedure.

The present invention provides a serum-free medium that is suitable for cultivation of a virus producer cell. Using the medium of the present invention, a virus producer cell can be efficiently cultivated under serum-free conditions, and a virus vector free of a serum can be produced with a procedure more convenient than a conventional one.

What is claimed is:

1. A serum-free medium used for cultivation of a virus producer cell, comprising:
    (a) human serum albumin at a concentration of 0.05 to 1% by weight;
    (b) calcium at a concentration of 2.70 to 4.51 mmol/L; and
    (c) a virus producer cell.

2. The medium according to claim 1, further comprising interleukin-2.

3. The medium according to claim 2, wherein interleukin-2 is at a concentration of 10 to 1000 JRU/ml.

4. The medium according to claim 1, further comprising epidermal growth factor.

5. The medium according to claim 1, wherein the virus producer cell is a recombinant retrovirus vector producer cell.

6. A method for producing a substance of interest, the method comprising cultivating a cell capable of producing a substance of interest in the medium defined by claim 1 to produce said substance of interest.

7. The method according to claim 6, wherein the cultivation is initiated by inoculating a stock of the cell capable of producing the substance of interest into said medium.

8. The method according to claim 6, wherein the substance of interest is a recombinant retrovirus vector.

* * * * *